US011937945B2

(12) United States Patent
Sheth

(10) Patent No.: US 11,937,945 B2
(45) Date of Patent: Mar. 26, 2024

(54) CATHETER WITH CAPACITIVE FORCE SENSOR

(71) Applicant: BIOSENSE WEBSTER (ISRAEL) LTD., Yokneam (IL)

(72) Inventor: Piyush Sheth, Porter Ranch, CA (US)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 0 days.

(21) Appl. No.: 17/717,668

(22) Filed: Apr. 11, 2022

(65) Prior Publication Data
US 2022/0233147 A1 Jul. 28, 2022

Related U.S. Application Data

(62) Division of application No. 15/986,730, filed on May 22, 2018, now Pat. No. 11,298,082.

(51) Int. Cl.
*A61B 18/14* (2006.01)
*A61B 5/00* (2006.01)
(Continued)

(52) U.S. Cl.
CPC .......... *A61B 5/6885* (2013.01); *A61B 5/6853* (2013.01); *A61B 5/6857* (2013.01); *A61B 18/1492* (2013.01); *A61M 25/10* (2013.01); *A61B 2018/00285* (2013.01); *A61B 2018/00357* (2013.01); *A61B 2018/00375* (2013.01);
(Continued)

(58) Field of Classification Search
CPC ... A61B 5/6885; A61B 5/6853; A61B 5/6857; A61B 2018/1492; A61B 2090/064; A61B 2090/065; A61B 2018/00285; A61B 2018/00357; A61B 2018/00375; A61B 2018/00577; A61B 2018/00839; A61B 2018/0022
See application file for complete search history.

(56) References Cited

U.S. PATENT DOCUMENTS 6,012,457 A 1/2000 Lesh
6,024,740 A 2/2000 Lesh et al.
(Continued)

OTHER PUBLICATIONS

European Search Report for corresponding EPA No. 19175704.6 dated Jan. 23, 2020.

*Primary Examiner* — Eun Hwa Kim
(74) *Attorney, Agent, or Firm* — Lewis Roca Rothgerber Christie LLP

(57) ABSTRACT

An electrophysiology catheter has a micro capacitive tactile sensor provided in the distal section. The distal section may include a tip electrode, a ring electrode and/or a balloon catheter adapted for tissue contact. The capacitive force sensor is configured to exhibit a change in capacitance with tissue contact wherein the force applied with tissue contact is measured and reliably calibrated in assessing and determining the applied force. The capacitive force sensor has a first plate affixed to a tissue contact portion of the catheter, a second plate configured for contact with the tissue, and an elastically compressible dielectric between the first and second plates, wherein the force sensor has a first capacitance when the first and second plates are separated by a first distance, and the force sensor has a second capacitance when the first and second plates are separated by a second different from the first distance.

12 Claims, 15 Drawing Sheets

(51) Int. Cl.
*A61M 25/10* (2013.01)
*A61B 18/00* (2006.01)
*A61B 90/00* (2016.01)
*A61M 25/00* (2006.01)

(52) U.S. Cl.
CPC ............... *A61B 2018/00577* (2013.01); *A61B 2018/00839* (2013.01); *A61B 2018/1435* (2013.01); *A61B 2090/065* (2016.02); *A61B 2218/002* (2013.01); *A61M 2025/0002* (2013.01); *A61M 2025/105* (2013.01); *A61M 2210/125* (2013.01)

(56) References Cited

U.S. PATENT DOCUMENTS

| | | | |
|---|---|---|---|
| 6,814,733 B2 | 11/2004 | Schwartz et al. | |
| 6,955,675 B2 | 10/2005 | Jain | |
| 7,340,307 B2 | 3/2008 | Maguire et al. | |
| 7,591,816 B2 | 9/2009 | Wang et al. | |
| 8,048,063 B2 | 11/2011 | Aeby et al. | |
| 8,998,893 B2 | 4/2015 | Avitall | |
| 9,757,050 B2 | 9/2017 | Ghaffari et al. | |
| 2002/0123749 A1 | 9/2002 | Jain | |
| 2008/0161796 A1* | 7/2008 | Cao | A61B 18/1492 606/41 |
| 2010/0168620 A1* | 7/2010 | Klimovitch | A61B 5/6885 600/587 |
| 2011/0227872 A1 | 9/2011 | Huska et al. | |
| 2012/0283715 A1 | 11/2012 | Mihalik et al. | |
| 2012/0283915 A1 | 11/2012 | Young et al. | |
| 2012/0330190 A1 | 12/2012 | Gliner | |
| 2014/0276783 A1 | 9/2014 | Srivastava | |
| 2015/0272669 A1* | 10/2015 | Brucker | A61B 18/1492 606/41 |
| 2015/0320472 A1 | 11/2015 | Ghaffari et al. | |
| 2016/0113712 A1 | 4/2016 | Cheung et al. | |
| 2016/0129223 A1 | 5/2016 | Kirschenman | |
| 2016/0175041 A1 | 6/2016 | Govari et al. | |
| 2020/0229866 A1 | 7/2020 | Harlev et al. | |

* cited by examiner

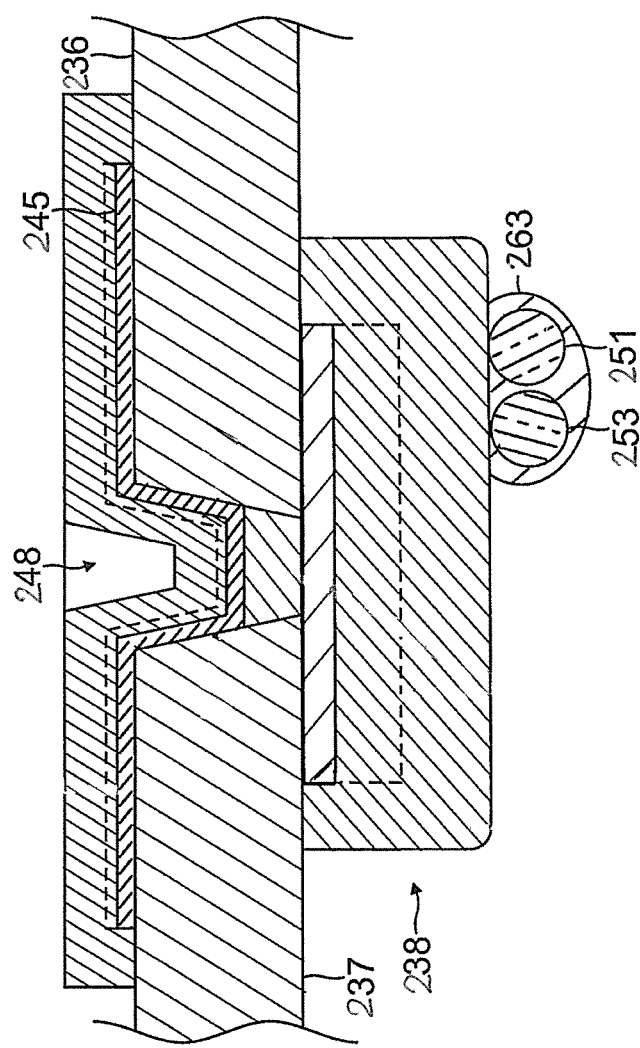

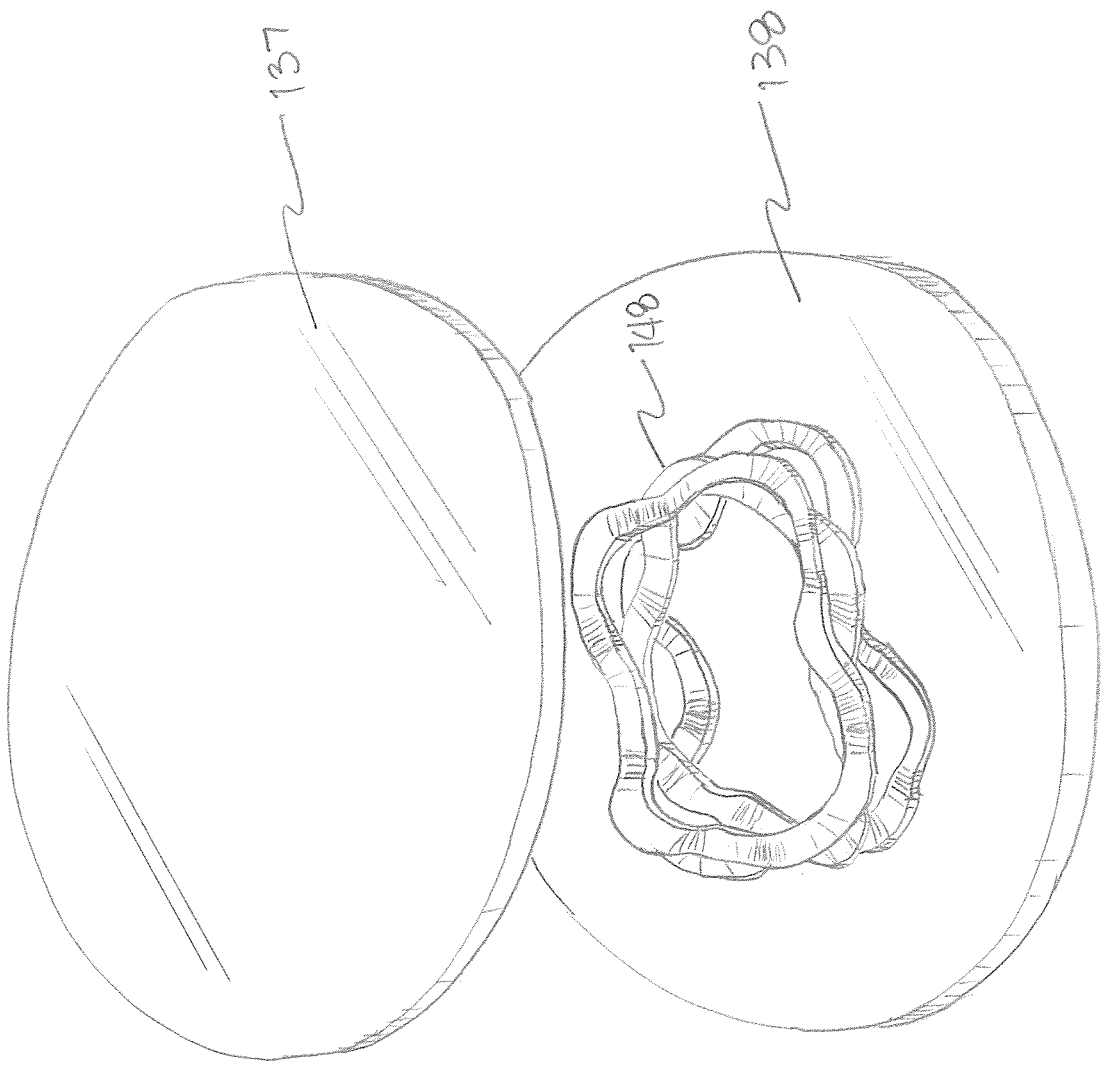

CATHETER WITH CAPACITIVE FORCE SENSOR

CROSS-REFERENCE TO RELATED APPLICATION(S)

This application is a divisional of and claims priority to U.S. patent application Ser. No. 15/986,730, filed May 22, 2018, now U.S. Pat. No. 11,298,082, the entire content of which is incorporated herein by reference.

FIELD OF INVENTION

This invention relates to medical devices. More particularly, this invention relates to improvements in cardiac catheterization, including electrophysiologic (EP) catheters, in particular, EP catheters for mapping and/or ablating ostia and tubular regions in the heart.

BACKGROUND

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Circumferential lesions at or near the ostia of the pulmonary veins have been created to treat atrial arrhythmias. U.S. Pat. Nos. 6,012,457 and 6,024,740, both to Lesh, disclose a radially expandable ablation device, which includes a radiofrequency electrode. Using this device, it is proposed to deliver radiofrequency energy to the pulmonary veins in order to establish a circumferential conduction block, thereby electrically isolating the pulmonary veins from the left atrium.

U.S. Pat. No. 6,814,733 to Schwartz et al., which is commonly assigned herewith and herein incorporated by reference, describes a catheter introduction apparatus having a radially expandable helical coil as a radiofrequency emitter. In one application the emitter is introduced percutaneously, and transseptally advanced to the ostium of a pulmonary vein. The emitter is radially expanded, which can be accomplished by inflating an anchoring balloon about which the emitter is wrapped, in order to cause the emitter to make circumferential contact with the inner wall of the pulmonary vein. The coil is energized by a radiofrequency generator, and a circumferential ablation lesion is produced in the myocardial sleeve of the pulmonary vein, which effectively blocks electrical propagation between the pulmonary vein and the left atrium.

Another example is found in U.S. Pat. No. 7,340,307 to Maguire, et al., which proposes a tissue ablation system and method that treats atrial arrhythmia by ablating a circumferential region of tissue at a location where a pulmonary vein extends from an atrium. The system includes a circumferential ablation member with an ablation element and includes a delivery assembly for delivering the ablation member to the location. The circumferential ablation member is generally adjustable between different configurations to allow both the delivery through a delivery sheath into the atrium and the ablative coupling between the ablation element and the circumferential region of tissue.

More recently, inflatable catheter electrode assemblies have been constructed with flex circuits to provide the outer surface of the inflatable electrode assemblies with a multitude of very small electrodes. Examples of catheter balloon structures are described in U.S. Publication No. 2016/0175041, titled Balloon for Ablation Around Pulmonary Vein, the entire content of which is incorporated herein by reference.

Flex circuits or flexible electronics involve a technology for assembling electronic circuits by mounting electronic devices on flexible plastic substrates, such as polyimide, Liquid Crystal Polymer (LCP), PEEK or transparent conductive polyester film (PET). Additionally, flex circuits can be screen printed silver circuits on polyester. Flexible printed circuits (FPC) are made with a photolithographic technology. An alternative way of making flexible foil circuits or flexible flat cables (FFCs) is laminating very thin (0.07 mm) copper strips in between two layers of PET. These PET layers, typically 0.05 mm thick, are coated with an adhesive which is thermosetting, and will be activated during the lamination process. Single-sided flexible circuits have a single conductor layer made of either a metal or conductive (metal filled) polymer on a flexible dielectric film. Component termination features are accessible only from one side. Holes may be formed in the base film to allow component leads to pass through for interconnection, normally by soldering.

Because the quality of a lesion depends on a number of factors, including size and depth, the force at which an electrode contacts tissue is a useful to a medical professional when ablating tissue. And because an ablating electrode has many possible configurations, including a tip electrode, a ring electrode or an electrode on a balloon, a force sensor should be adaptable for use with any such electrodes, so that force can be measured whether tissue contact occurs at a catheter's distal tip as a point contact on tissue or its side while being dragged along tissue, or even simultaneously at multiple tissue surface locations circumferentially within an ostium or tubular region.'

Accordingly, there is a desire for a catheter having an electrode with a force sensor that is configured for measuring a force applied by the electrode against tissue surface. And because a capacitive tactile sensor is reliably responsive to the an applied force and can be manufactured in very small sizes, an electrode having a capacitive force sensor can reliably measure an applied force whether the electrode is configured as a tip electrode, a ring electrode or even as an electrode on a balloon catheter.

SUMMARY OF THE INVENTION

The present invention is directed to an electrophysiology catheter with a micro capacitive tactile sensor provided in the distal section where tissue contact occurs, wherein the distal section may include a tip electrode, a ring electrode and/or a balloon catheter. The capacitive sensor is configured to exhibit a change in capacitance upon touching tissue and during tissue contact wherein the force applied with tissue contact is measured and reliably calibrated in assessing and determining the applied force.

In some embodiments, the catheter has an elongated catheter shaft, a distal tip electrode having a shell configured for contact with tissue and a capacitive force sensor having a first plate affixed to the shell, a second plate distal of the first plate and configured for contact with the tissue, and an elastically compressible dielectric between the first and second plates, wherein the force sensor has a first capacitance when the first and second plates are separated by a first distance, and the force sensor has a second capacitance when the first and second plates are separated by a second different from the first distance. The catheter also includes a first terminal connected to the first plate, and a second terminal connected to the second plate.

In some embodiments, the first and second plates are parallel to each other.

In some embodiments, the first and second plates are generally of the same size and shape.

In some embodiments, the capacitive force sensor is affixed to a distal face of the shell.

In some embodiments, the first plate protrudes above an outer surface of the shell.

In some embodiment, the shell has a recess and the capacitive force sensor is situated in the recess with at least the first plate exposed.

In some embodiments, the recess is formed in a distal face of the shell.

In some embodiments, the recess is formed in a circumferential wall of the shell.

In some embodiments, the first terminal passes through a first through-hole formed in the shell.

In some embodiments, the second terminal passes through a second through-hole formed in the shell.

In some embodiments, the first terminal extends along an outer surface of the shell.

In some embodiments, an electrophysiology catheter adapted for use in an ostium, includes a balloon having an membrane and configured with a distal end and a proximal end defining a longitudinal axis and at least one circumferential latitude, and a micro capacitive force sensor having a first plate on the balloon, a second plate configured for contact with the tissue, and an elastically compressible dielectric between the first and second plates, wherein the force sensor has a first capacitance when the first and second plates are separated by a first distance, and the force sensor has a second capacitance when the first and second plates are separated by a second different from the first distance. The catheter also has a first terminal connected to the first plate, and a second terminal connected to the second plate.

In some embodiments, the first plate is affixed to the membrane.

In some embodiments, the catheter also includes a contact electrode and the first plate is affixed to the contact electrode.

In some embodiments, the contact electrode is configured with an elongated body and a plurality of transverse members.

In some embodiments, the catheter also includes a first via through the membrane, wherein the first terminal is connected to the first via.

In some embodiments, the catheter also includes a second via through the membrane, the second terminal connected to the second via.

In some embodiments, the catheter includes a plurality of capacitive force sensors arranged along a circumferential latitude of the balloon.

In some embodiments, an electrophysiology catheter system having a catheter having a capacitive force sensor with has a first plate, a second plate, and a dielectric therebetween, and a processor having a memory device and a voltage source. The catheter also includes a first terminal connected to the first plate and the voltage source, and a second terminal connected to the second plate and the voltage source, wherein the memory device is configured to store instructions that, when executed by the processor, causes the processor to: actuate the voltage source, determine a capacitance across the capacitive force sensor, and detect a change in the capacitance.

In some embodiments, the capacitive force sensor has a first capacitance when the first and second plates are separated by a first distance, and the capacitive force sensor has a second capacitance when the first and second plates are separated by a second distance, and the processor is configured to detect the change in capacitance between the first and second capacitance.

In some embodiments, the dielectric is compressible.

In some embodiments, the dielectric is elastically compressible.

In some embodiments, the capacitive force sensor is positioned on a distal portion of the catheter configured for tissue contact.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 10B is a side cross-sectional view of a via formed in a balloon membrane, according to an embodiment of the present invention.

FIG. 12 is a detailed, exploded perspective view of a capacitive force sensor, according to another embodiment of the present invention.

DETAILED DESCRIPTION OF THE INVENTION

System Description

Figure 1:
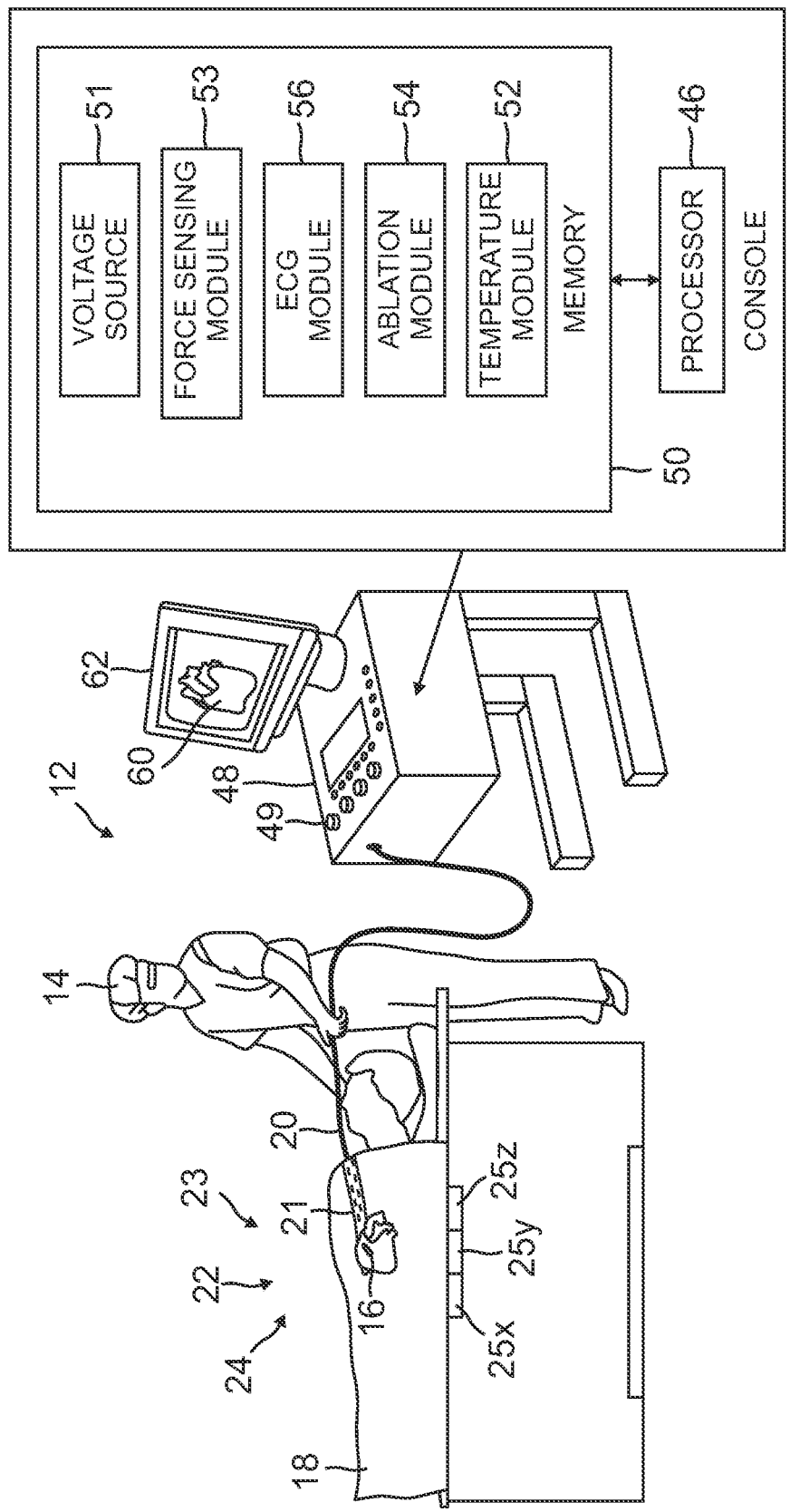
FIG. 1 is a schematic illustration of a medical procedure, according to an embodiment of the present invention.

In the following description, like elements in the drawings are identified by like numerals, and like elements are differentiated as necessary by appending a letter to the identifying numeral.

FIG. 1 is a schematic illustration of an invasive medical procedure using apparatus 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it is understood that embodiments of the present invention are not merely applicable to this specific procedure, and may include substantially any procedure on biological tissue or on non-biological materials.

In order to perform the ablation, medical professional 14 inserts a probe 20 into a sheath 21 that has been pre-positioned in a lumen of the patient. Sheath 21 is positioned so that a distal end 22 of probe 20 enters the heart of the patient. A catheter 24, which is described in more detail below, is deployed through a lumen 23 of the probe 20, and exits from a distal end of the probe 20.

As shown in FIG. 1, apparatus 12 is controlled by a system processor 46, which is located in an operating console 15 of the apparatus. Console 15 comprises controls 49 which are used by professional 14 to communicate with the processor. During the procedure, the processor 46 typically tracks a location and an orientation of the distal end 22 of the probe 20, using any method known in the art. For example, processor 46 may use a magnetic tracking method, wherein magnetic field generators 25X, 25Y and 25Z external to the patient 18 generate signals in coils positioned in the distal end of the probe 20. The CARTO® available from Biosense Webster, Inc. of Diamond Bar, California, uses such a tracking method.

The software for the processor 46 may be downloaded to the processor in electronic form, over a network, for example. Alternatively or additionally, the software may be provided on non-transitory tangible media, such as optical, magnetic, or electronic storage media. The tracking of the distal end 22 is typically displayed on a three-dimensional representation 60 of the heart of the patient 18 on a screen 62.

In order to operate apparatus 12, the processor 46 communicates with a memory 50, which has a number of modules used by the processor to operate the apparatus. Thus, the memory 50 comprises a temperature module 52, an ablation module 54, and an electrocardiograph (ECG) module 56. The memory 50 typically comprises other modules, such as a force sensor module 53, with a voltage source 51, for sensing the force on the distal end 22. The memory 50 may also include a tracking module 55 for operating the tracking method used by the processor 46, and an irrigation module 57 allowing the processor to control irrigation provided for the distal end 22. The modules may comprise hardware as well as software elements.

Catheter

Figure 2:
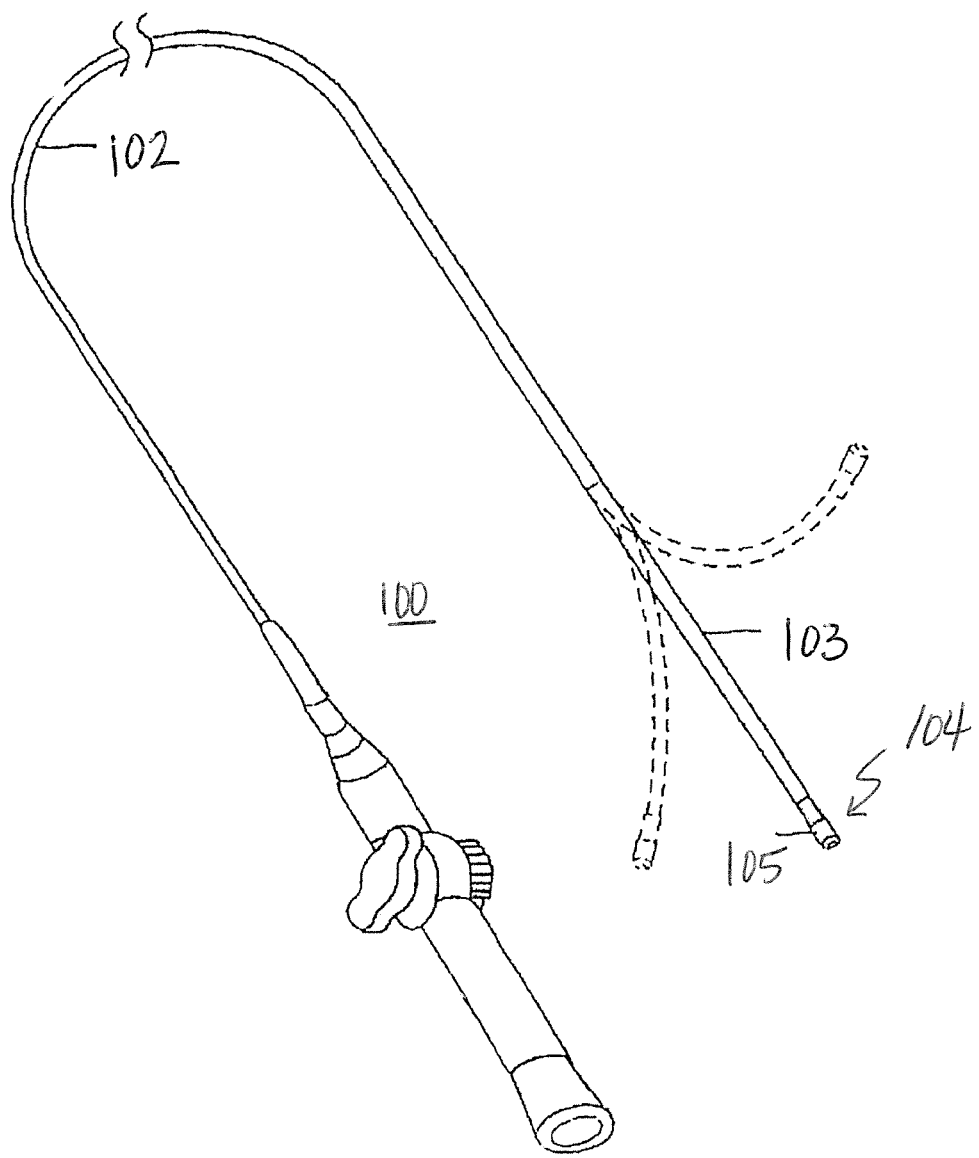
FIG. 2 is a perspective view of a catheter suitable for use in the medical procedure of FIG. 1, according to an embodiment of the present invention.
Figure 3:
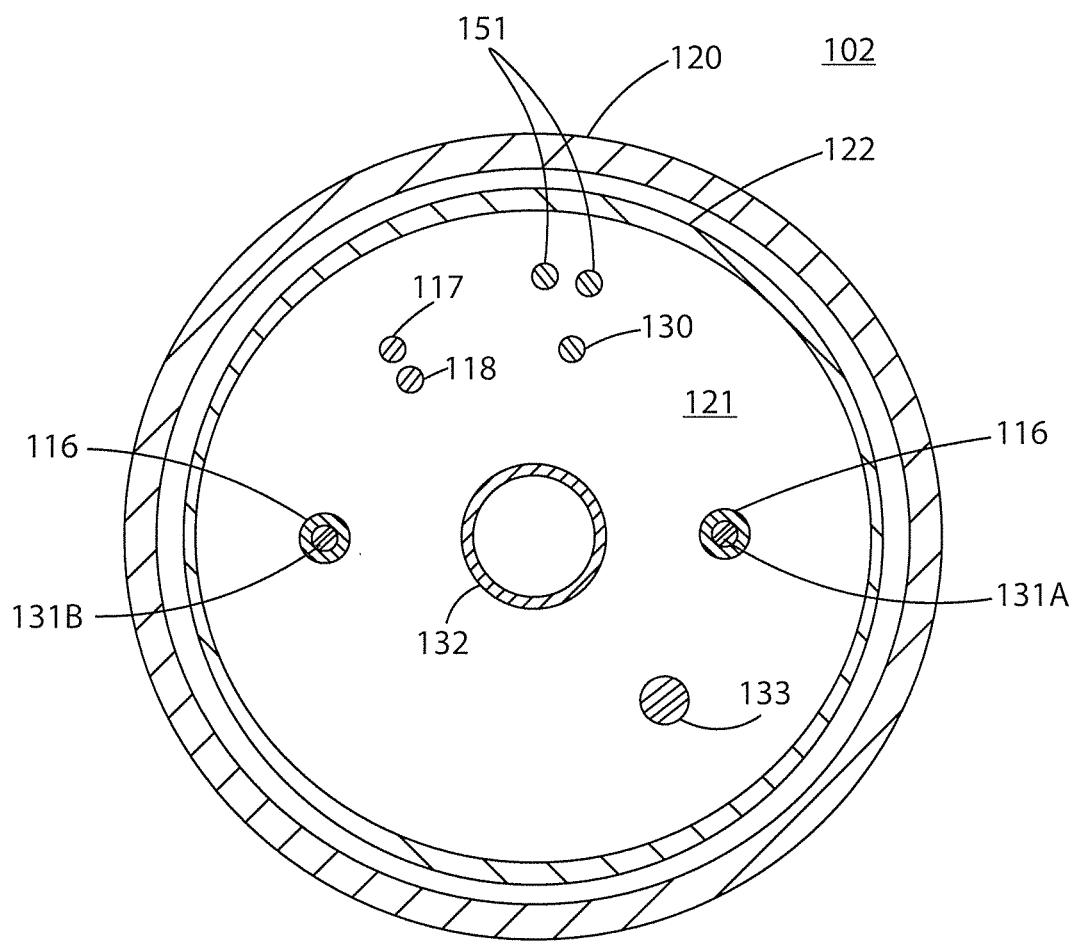
FIG. 3 is an end cross-sectional view of a catheter body of the catheter of FIG. 2.

FIG. 2 is a schematic perspective view of a catheter 100 suitable for use with the aforementioned apparatus 12. The catheter 100 has an elongated catheter body 102, a deflection section 103 and a distal section 104 which includes a distal tip electrode 105. As understood in the art, in some embodiments, the catheter body 102 has an outer wall 120 with a central lumen 121, which may be lined with a stiffener tubing 122, as shown in FIG. 3. Various components pass through the lumen 121, including, for example, lead wires 130 for the tip electrode 105 and any ring electrodes (not shown), a pair of deflection puller wires (or tensile members) 131A, 131B, an irrigation tubing 132, a cable 133 for an EM position sensor (not shown) housed in the distal section 104, thermocouple wire or wire pair 151/153, and any other cables or wires.

Figure 4:
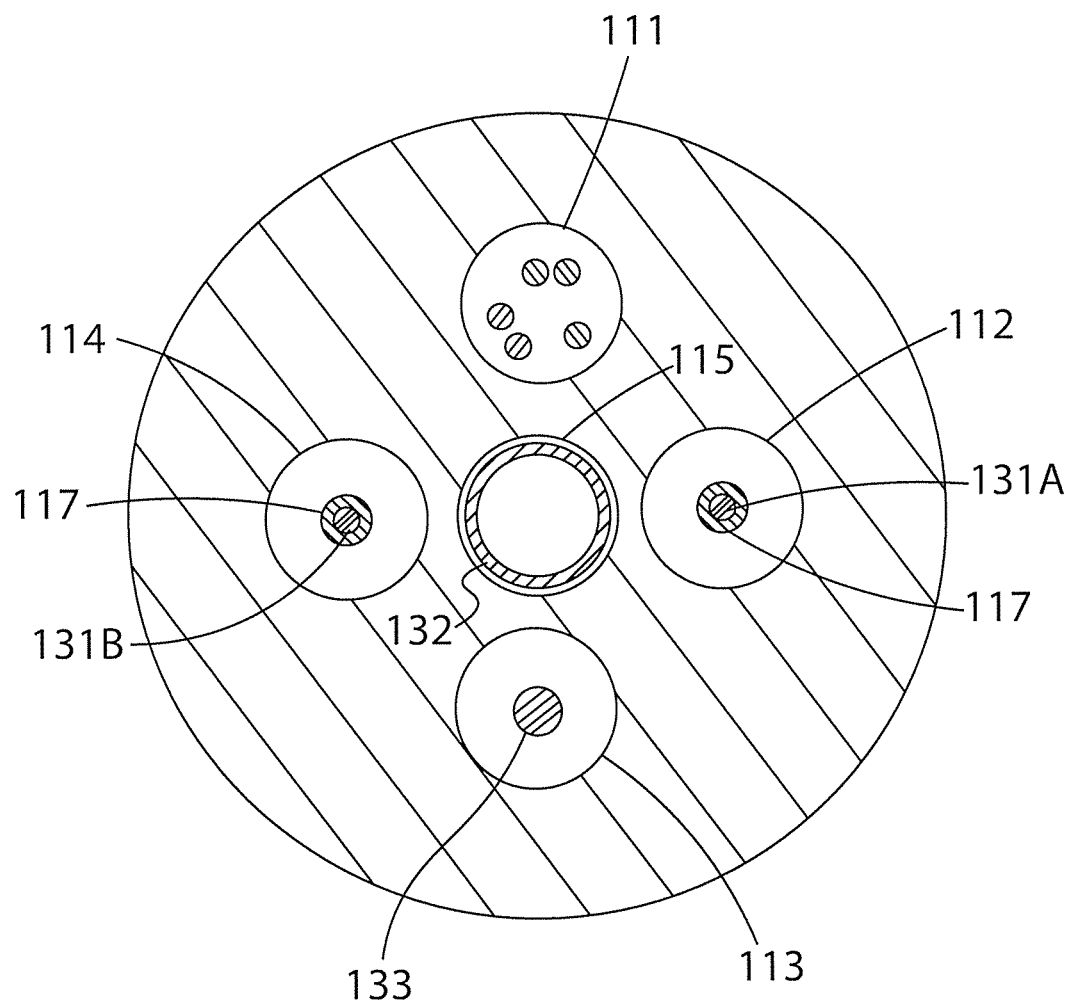
FIG. 4 is an end cross-sectional view of a deflection section of the catheter of FIG. 2.

As understood in the art, in some embodiments, the deflection section 103 includes a shorter section of multi-lumened tubing 110 with multiple lumens. As shown in FIG. 4, the lumens include, for example, a first lumen 111 for the lead wires 130 and thermocouple wire or wire pair 151/153, a second lumen 112 for the first puller wire 131A, a third lumen 113 for the cable 133, a fourth lumen 114 for the second puller wire 131B, and a fifth lumen 115 for the irrigation tubing 132. The size, shape and location of the lumens are not critical, except that the second and fourth lumens 122 and 124 may be off-axis and diametrically opposed for effective bi-directional deflection of the deflection section 103. As understood in the art, portions of the puller wires 131A, 131B extending through the catheter body 102 are surrounded by respective compression coils 116 which generally limit deflection curvature of the catheter to the multi-lumened tubing 110 of the deflection section 103, distal of the catheter body 102. Portions of the puller wires 131A, 131B distal of the catheter body 102 are surrounded by respective protective sheaths 117 which prevent the puller wires from cutting into the side wall of the multi-lumened tubing 110 when the deflection section 103 is deflected.

Figure 5A:
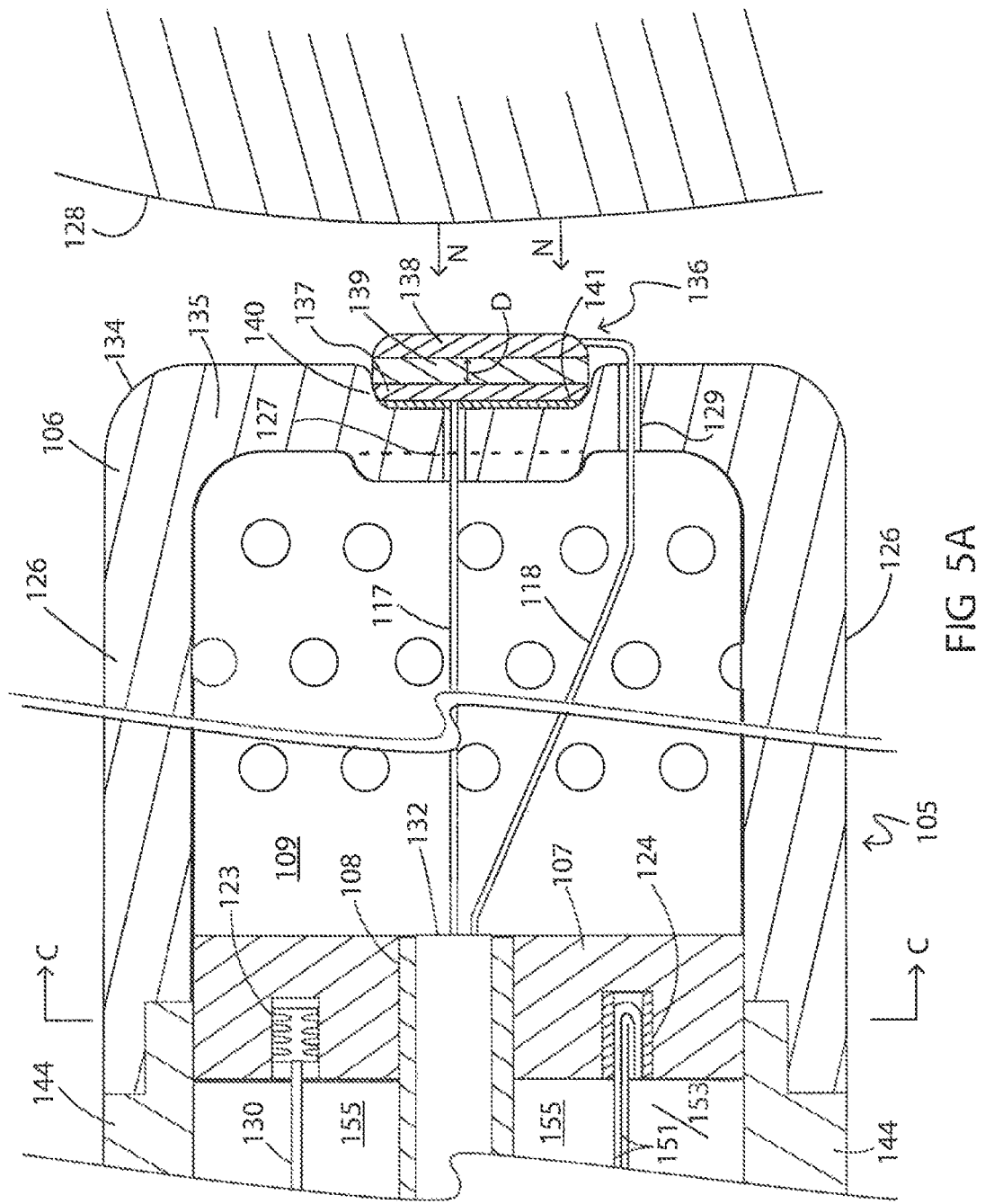
FIG. 5A is side cross-sectional view of a distal section of the catheter of FIG. 2, including a distal tip electrode with a capacitive force sensor in a neutral configuration.

As shown in FIG. 5A. the tip electrode 105 of the distal section 104 has a shell 106 and a plug 107 defining an interior chamber 109 through which irrigation fluid enters the interior chamber 109 via a distal end section of the irrigation tubing 132 that passes through the plug 107 via a through-hole 108. A distal end of lead wire 130 for tip electrode 105 terminates in a blind hole 123 formed in a proximal face of the plug 107. Distal ends of thermocouple wire(s) 151/153 terminate in a blind hole 124 formed in the proximal face of the plug 107.

Figure 5B:
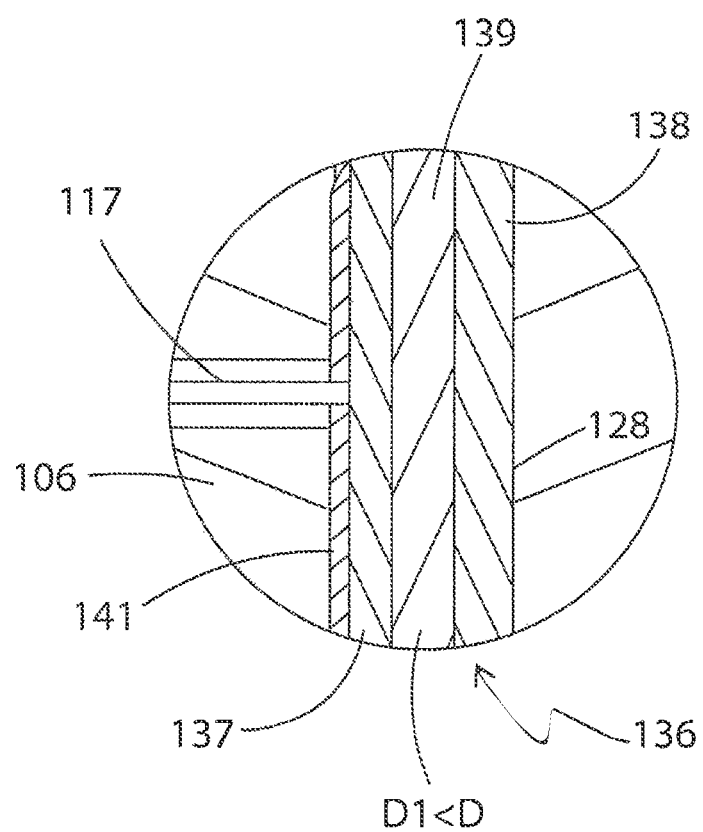
FIG. 5B is a detailed cross-sectional view of the capacitive force sensor of FIG. 5A in a tissue contact or compressed configuration.

On an outer surface 134 of a distal wall 135 of the shell 106, a capacitive force sensor 136 is provided to sense the application of a force, including a force with any normal component, on the distal wall 135, for example, when the distal wall 135 comes into contact with tissue surface 128 (see FIG. 5B). The capacitive force sensor 136 is situated in a recess 140 formed in the distal wall 135, for example, by stamping (solid line) or shallow boring (broken line), and has two conductive plates 137, 138 and a dieletric 139 in between. It is understood that the recess 140 may also be formed in a circumferential sidewall 126 of the shell 106 for tissue contact when the distal section 104 lays against tissue and is dragged along the tissue surface.

In some embodiments, the plates are of similar construction in shape and size and are generally parallel to each other. With the plates 137 and 138 separated from each other by a distance D when the capacitive force sensor 136 is in its neutral state, the capacitive force sensor 136 has a thickness T while in its neutral state, free from any forces or contact. However, the dielectric has an elastic structure allowing deformation, including compression between the plates when the capacitive force sensor 136 is subjected to a force with a vector component perpendicular to the distal wall 135 of the tip shell 106. Advantageously, the capacitance of the force sensor 136 changes when the distance between the plates 137 and 138 changes. In particular, the capacitance of the force sensor 136 increases when the distance between the plates decreases.

As shown in FIG. 5A, the inner plate 137 is affixed to surface 134 in the recess 140, for example, by adhesive 141, and in some embodiments, the plates 137 and 138 are generally parallel to the distal wall 135. The depth of the recess 140 is less than the thickness T of the capacitive force sensor 136 in its neutral state so that the outer plate 138 is projected out in front of the distal wall 135 and is exposed so that it can be pressed toward the plate 137 upon contact with the tissue surface 128 when the catheter is advanced toward the tissue surface for mapping and/or ablation.

Figure 5C:
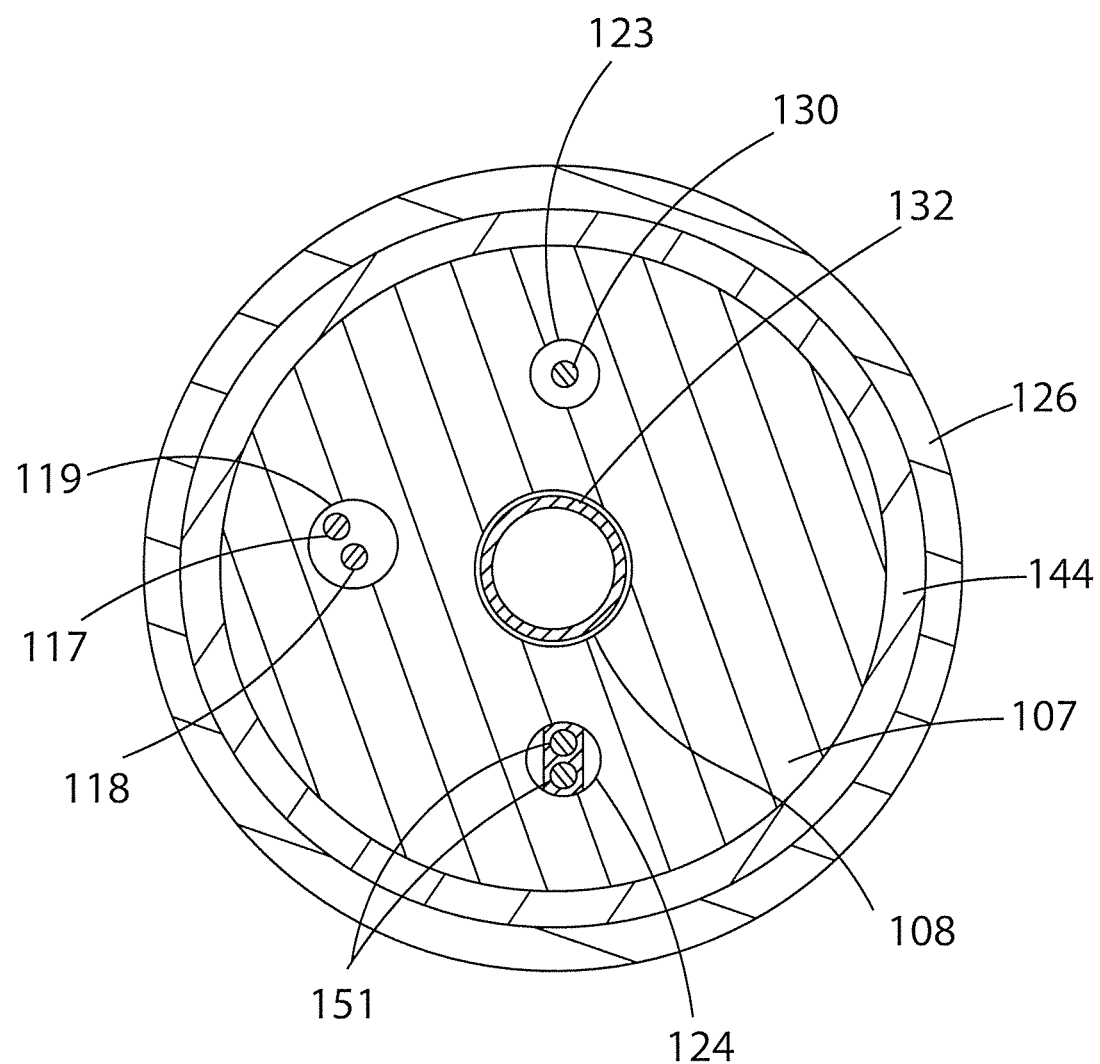
FIG. 5C is an end cross-sectional view of a proximal end of the distal tip electrode of FIG. 5A, taken along line C-C.

The first plate 137 is connected to a first terminal 117 and the second plate is connected to a second terminal 118, each of which may take the form of a lead wire that passes through respective apertures 127 and 129 formed in the distal wall 135 of the shell 106. The terminals 117 and 118, appropriately protected by insulating sheaths (not shown), extend through the interior chamber 109 and a common or different through-hole(s) 119 formed in the plug 107 (see FIG. 5C). In some embodiments, a short, single-lumened connector tubing 144 extends between the distal end of the multi-lumened tubing 110 and the tip electrode 105, to allow components to reorient as needed between their respective lumen and their respective blind holes or through-holes in the plug 107 of the tip electrode 105.

In use, the capacitance of the force sensor 136 is measured by the force sensing module 53 of the operating console (see FIG. 1). A voltage is applied across the capacitive force sensor 136 by the voltage source 51 of the force sensing module 53 via the terminals 117, 118. The capacitance for the force sensor 136 in the neutral state with the plates 137 and 138 separated by a distance D (see FIG. 5A) is measured by the force sensing module 53 as C. When the tip electrode 105 approaches tissue, the tissue surface 128 contacts protruding outer plate 138 and exerts a force with a normal force component N which compresses the dielectric 139 changing the separation distance from D to D1 (see FIG. 5B), where D1<D, which changes the capacitance of the force sensor 136 from C to C1, where C1>C. The force sensing module 53 detects the increase capacitance C1 and, for example, responds by providing an indicia to the medical professional 14, such as activating an audio signal and/or a visual signal. The measured capacitance remains at C1 so long as the normal force component N remains. Where the normal force component increases (such as where the medical professional further presses the distal tip electrode into the tissue surface), the separation distance decreases further to D2 where D2<D1<D and the measured capacitance increases correspondingly to C2, where C2>C1>C. Where the normal force component decreases (such as where the medical professional begins to retract the distal trip electrode from the tissue surface, the separation distance increases to D3 where D1<D3<D, and the measured capacitance decreases correspondingly to C3, where C1>C3>C. In this manner, the change in the capacitance output of the force sensor 136 from C1 to C3 is detected and measured by the force sensor 136 which advantageously indicates the change in force applied to the tip electrode 105 that is reflective of the change in tissue contact between the tip electrode and tissue surface, for example, by changing the audio signal and/or the visual signal.

Figure 6:
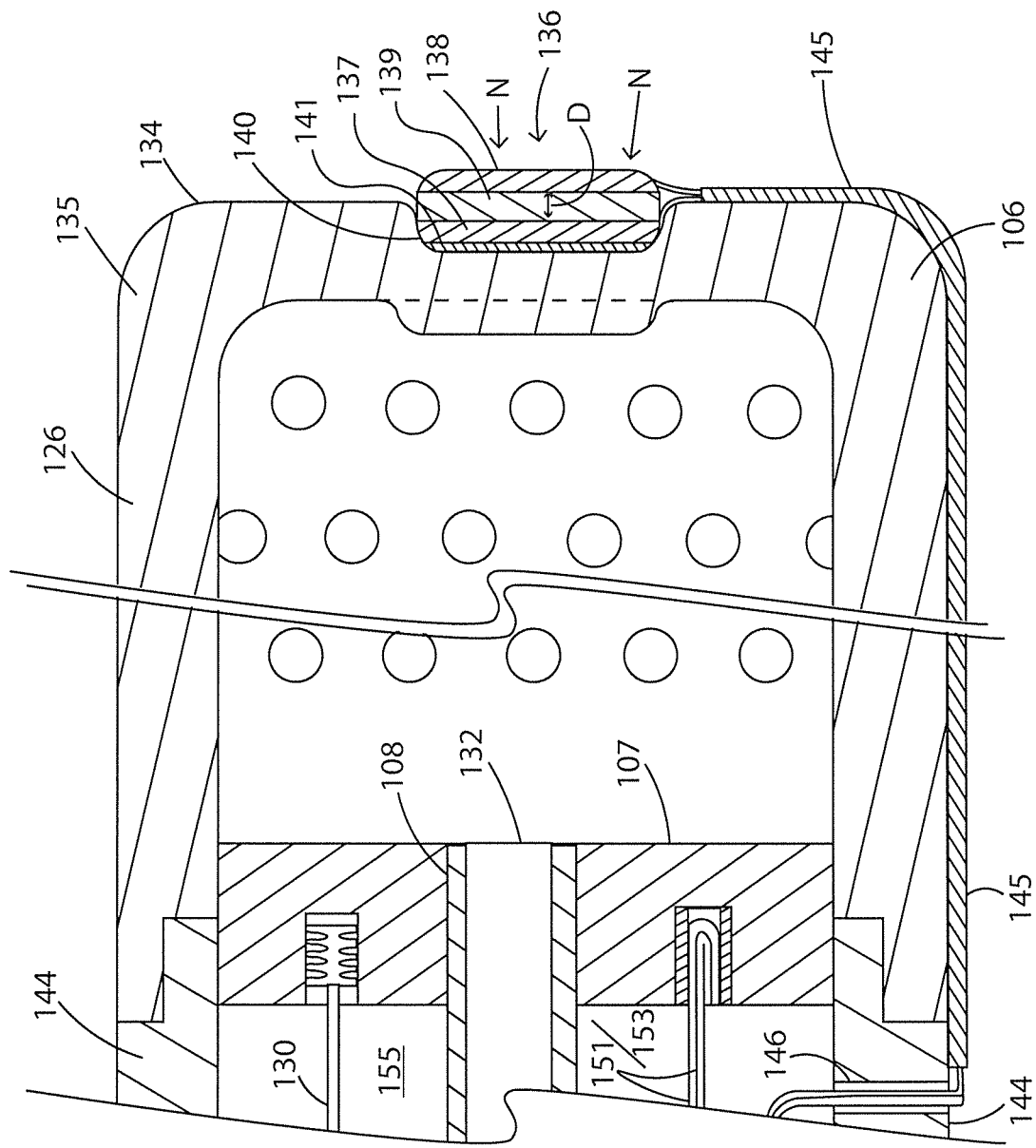
FIG. 6 is a side cross-sectional view of a distal section of a catheter, in accordance with another embodiment of the present invention.

In some embodiments, the terminals 117 and 118 are connected to electrical extensions (e.g., embedded lead wires, not shown) of a flex circuit 145 that is affixed to the outer surface 134 of the shell 106, as shown in FIG. 6. The flex circuit 145 or the embedded lead wires pass through one or more sealed through-holes 146 formed in the sidewall of the connector tubing 144 to enter into the lumen of the connector tubing 144 and proximally into an appropriate lumen of the multi-lumened tubing 110.

Figure 7:
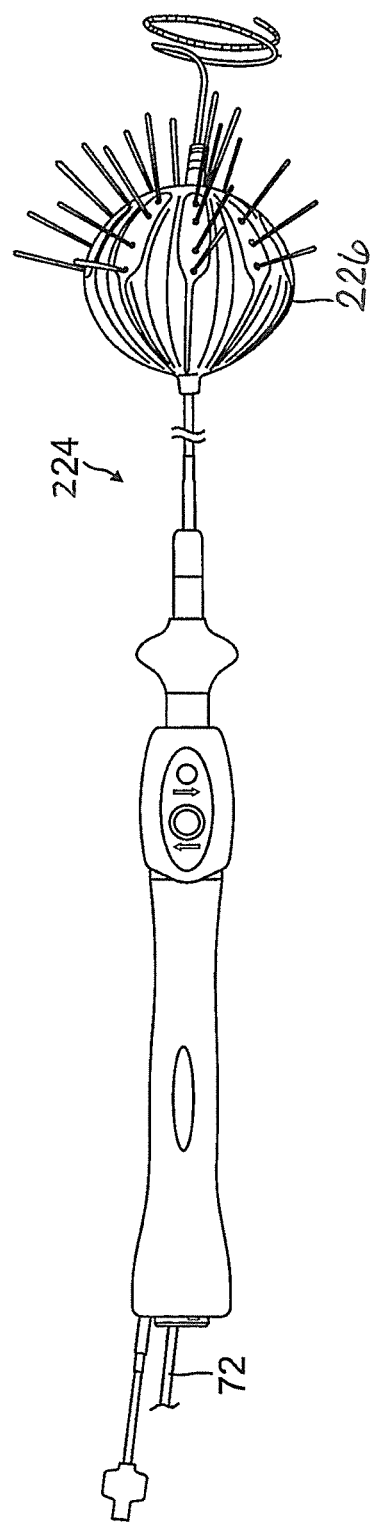
FIG. 7 is a top plan view of a balloon catheter suitable for use in the medical procedure of FIG. 1, according to another embodiment of the present invention.

In some embodiments, a catheter 224 has a distal inflatable member or balloon 280, as shown in FIG. 7 in an inflated deployed configuration. The balloon 280 is used to ablate an ostium 211 of a lumen, such as a pulmonary vein 213. The inflatable balloon 280 of the catheter 224 has an exterior wall or membrane 226 of a bio-compatible material, for example, formed from a plastic such as polyethylene terephthalate (PET), polyurethane or PEBAX®. The balloon 280 is deployed, in a collapsed uninflated configuration and may be inflated and deflated by injection and emission of a fluid such as saline solution through a shaft 270. The membrane 226 of the balloon 280 is formed with irrigation pores or apertures 227 through which the fluid can exit from the interior of the balloon 280 to outside the balloon for cooling the tissue ablation site at the ostium. While FIG. 7 shows fluid exiting the balloon as jet streams, it is understood that the fluid may exit the balloon with any desired flow rate and/or pressure, including a rate where the fluid is seeping out of the balloon. A suitable balloon is described in U.S. application Ser. No. 15/360,966, filed Nov. 23, 2016, the entire disclosure of which is incorporated herein by reference.

The membrane 226 supports and carries a combined electrode and temperature sensing member which is constructed as a multi-layer flexible circuit electrode assembly 284. The "flex circuit electrode assembly" 284 may have many different geometric configurations. In the illustrated embodiment of FIG. 8, the flex circuit electrode assembly 284 has a plurality of strips 230. The leaves 230 are generally evenly distributed about the distal end 288 and the balloon 280. One or more contact electrodes 233 on each leaf come into galvanic contract with the ostium 211 during an ablation procedure, during which electrical current flows from the contact electrodes 233 to the ostium 211 to form lesions 231.

Figure 9:
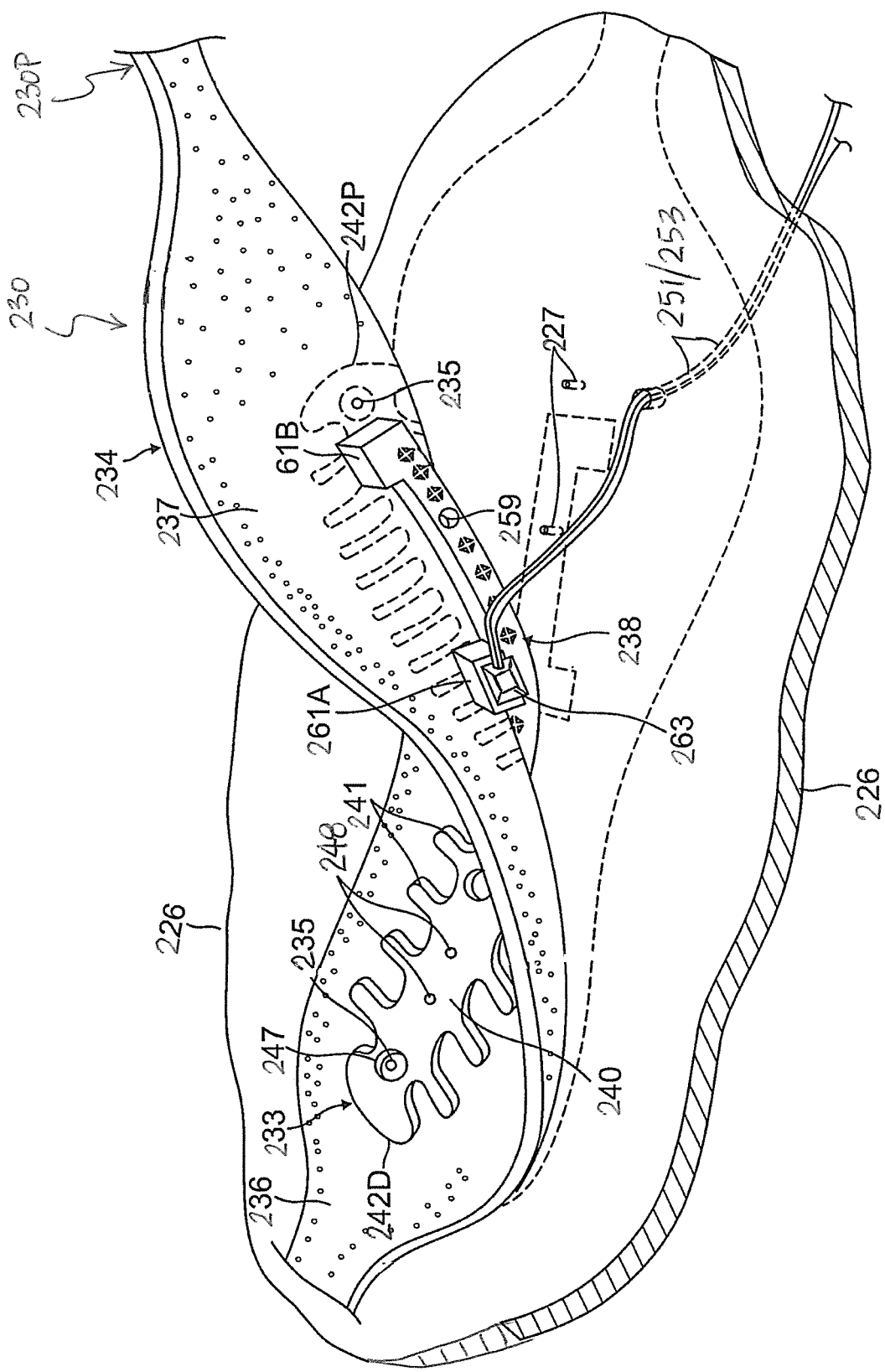
FIG. 9 is a perspective view of a flexible circuit electrode assembly partially lifted off the balloon to reveal its underside and related elements, according to an embodiment of the present invention.

For simplicity, the flex circuit electrode assembly 284 is described with respect to one of its leaf 230 as shown in FIG. 9, although it is understood that following description may apply to each leaf of the assembly. The flex circuit electrode assembly 284 includes a flexible and resilient sheet substrate 234, constructed of a suitable bio-compatible materials, for example, polyimide. In some embodiments, the sheet substrate 234 has a greater heat resistance (or a higher melting temperature) compared to that of the balloon membrane 226. In some embodiments, the substrate 234 is constructed of a thermoset material having a decomposition temperature that is higher than the melting temperature of the balloon membrane 226 by approximately 100 C or more.

The substrate 234 is formed with one or more irrigation pores or apertures 235 that are in alignment with the irrigation apertures 235 of the balloon membrane 226 so that fluid in the interior of the balloon can pass through the irrigation apertures 235 and exit the balloon to the ablation sites on the ostium.

Figure 10A:
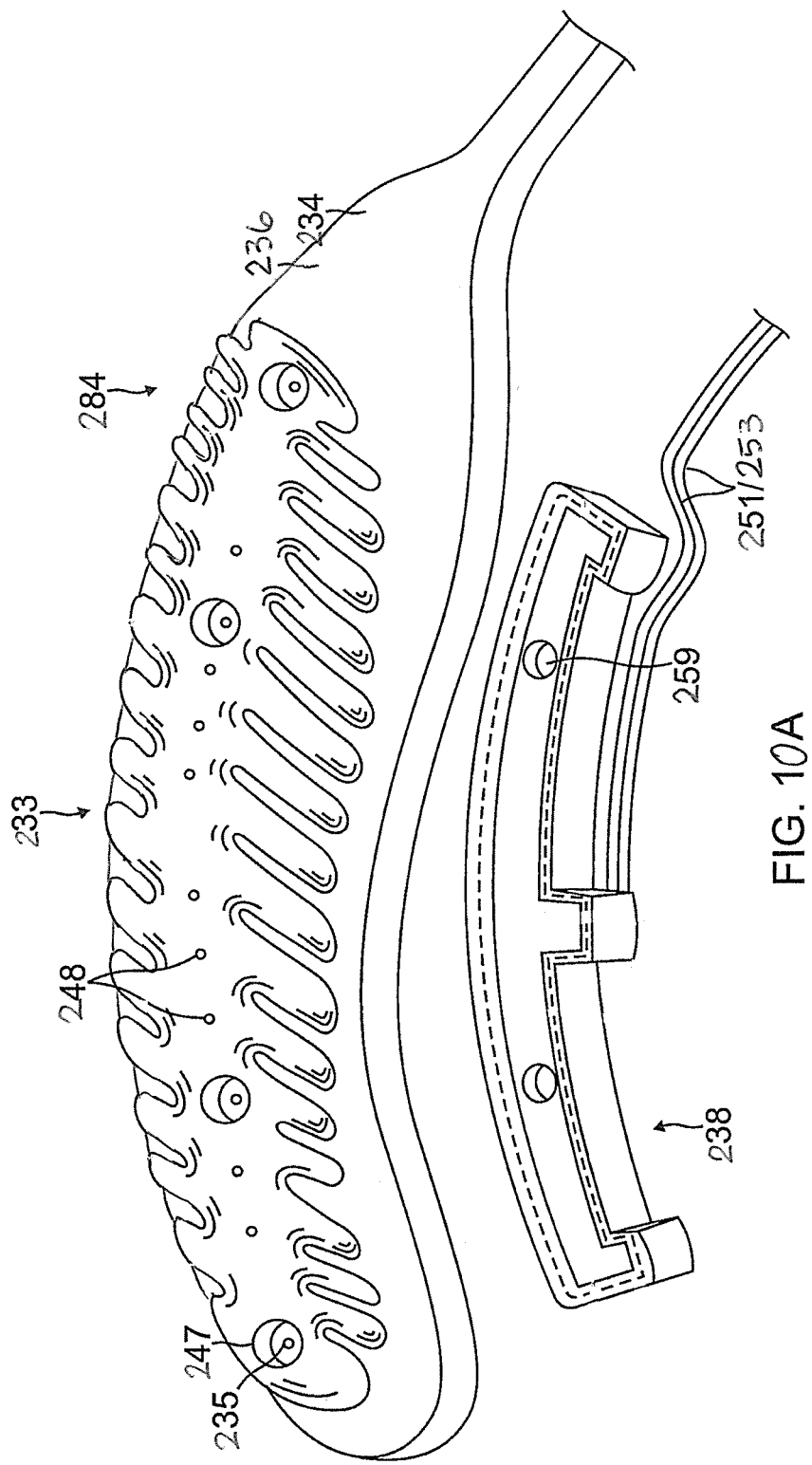
FIG. 10A is an exploded view of a flexible circuit electrode assembly during a stage of construction, according to an embodiment of the present invention.

The substrate 234 has a first or outer surface 236 facing away from the balloon membrane 226, and a second or inner surface 237 facing the balloon membrane 226. On its outer surface 236, the substrate 234 supports and carries the contact electrodes 233 adapted for tissue contact with the ostium. On its inner surface 237, the substrate 234 supports and carries a wiring electrode 238. The contact electrode 233 delivers RF energy to the ostium during ablation and/or is connected to a thermocouple junction for temperature sensing of the ostium. In the illustrated embodiment, the contact electrode 233 has a longitudinally elongated portion 240 and a plurality of thin transversal linear portions or fingers 241 extending generally perpendicularly from each lateral side of the elongated portion 240 between enlarged proximal and distal ends 242P and 242D, generally evenly spaced therebetween. The elongated portion 240 has a greater width and each of the fingers has a generally uniform lesser width. Accordingly, the configuration or trace of the contact electrode 233 resembles a "fishbone." In contrast to an area or "patch" ablation electrode, the fingers 241 of the contact electrode 233 advantageously increase the circumferential or equatorial contact surface of the contact electrode 233 with the ostium while void regions 243 between adjacent fingers 241 advantageously allow the balloon 280 to collapse inwardly and/or expand radially as needed at locations along its equator. In the illustrated embodiment, the fingers 241 have different lengths, some being longer, others being shorter For example, the plurality of fingers include a distal finger, a proximal finger and fingers therebetween, where each of the fingers in between has a shorter adjacent finger. For example, each finger has a length different from its distal and/or proximal immediately adjacent neighboring finger(s) such that the length of each finger generally follows the tapered configuration of each leaf 230. In the illustrated embodiment, there are 222 fingers extending across (past each lateral side of) the elongated portion 240, with the longest finger being the third finger from the enlarged proximal end 242P. In some embodiments, the contact electrode 233 includes gold 258B with a seed layer 245, between the gold 258B and the membrane 226 (see FIG. 10A and FIG. 10B). The seed layer may include titanium, tungsten, palladium, silver, and/or combinations thereof.

Formed within the contact electrode 233 are one or more exclusion zone 247, each surrounding an irrigation aperture 227 formed in the substrate 234. The exclusion zones 247 are voids purposefully formed in the contact electrode 233, as explained in detail further below, so as to avoid damage to the contact electrode 233 during construction of the electrode assembly 284 in accommodating the irrigation apertures 227 at their locations and in their function.

Also formed in the contact electrode 233 are one or more conductive blind vias 248 which are conductive or metallic formations that extend through through-holes (not shown) in the substrate 234 and are configured as electrical conduits connecting the contact electrode 233 on the outer surface 236 and the wiring electrode 238 on the inner surface 237. It is understood that "conductive" is used herein interchangeably with "metallic" in all relevant instances.

On the inner surface 237 of the substrate 234, the wiring electrode 238 is generally configured as an elongated body generally similar in shape and size to the elongated portion 240 of the contact electrode 233. The wiring electrode 238 loosely resembles a "spine" and also functions as a spine in terms of providing a predetermined degree of longitudinal rigidity to each leaf 230 of the electrode assembly 284. The wiring electrode 238 is positioned such that each of the blind vias 248 is in conductive contact with both the contact electrode 233 and the wiring electrode 238. In the illustrated embodiment, the two electrodes 233 and 238 are in longitudinal alignment with other, with all nine blind vias 248 in conductive contact with both electrodes 233 and 238. In some embodiments, the wiring electrode 238 has an inner portion of copper and an outer portion of gold.

The wiring electrode 238 is also formed with its exclusion zones 259 around the irrigation apertures 235 in the substrate 234. The wiring electrode 238 is further formed with solder pad portions 261, at least one active 261A, and there may be one or more inactive solder pad portions 261B. The solder pad portions 261A and 261B are extensions from a lateral side of the elongated body of the wiring electrode 238. In the illustrated embodiment, an active solder pad portion 261A is formed at about a mid-location along the elongated body, and a respective inactive solder pad portion 261B is provided at each of the enlarged distal end 242D and the enlarged proximal end 242P.

Attached, e.g., by a solder weld 263, to the active solder pad portion 261A are the wire pair, e.g., a constantan wire 251 and a copper wire 253. The copper wire 253 provides a lead wire to the wiring electrode 233, and the copper wire 253 and the constantan wire 251 provide a thermocouple whose junction is at solder weld 263. The wire pair 251/253 are passed through a through-hole 229 formed in the membrane 226 into the interior of the balloon 280. It is understood that, in other embodiments in the absence of the through-hole 229, the wire pair 251/253 may run between the membrane 226 and the substrate 234 and further proximally between the membrane 226 and a proximal tail 230P until the wire pair 251/253 enters the tubular shaft 270 via a through-hole (not shown) formed in the tubular shaft sidewall near its distal end.

The flex circuit electrode assembly 284, including the leaves 230 and the tail 230P, is affixed to the balloon membrane 226 such that the outer surface 236 of the substrate 234 is exposed and the inner surface 237 of the substrate 234 is affixed to the balloon membrane 226, with the wiring electrode 238 and wire pair 251/253 sandwiched between the substrate 234 and the balloon membrane 226. The irrigation apertures 235 in the substrate 234 are aligned with the irrigation apertures 227 in the balloon membrane 226. The exclusion zones 259 in the wiring electrode 238 and the exclusion zones 247 in the contact electrode 233 are concentrically aligned with each other, as well as with the irrigation apertures 227 and 235.

Figure 8:
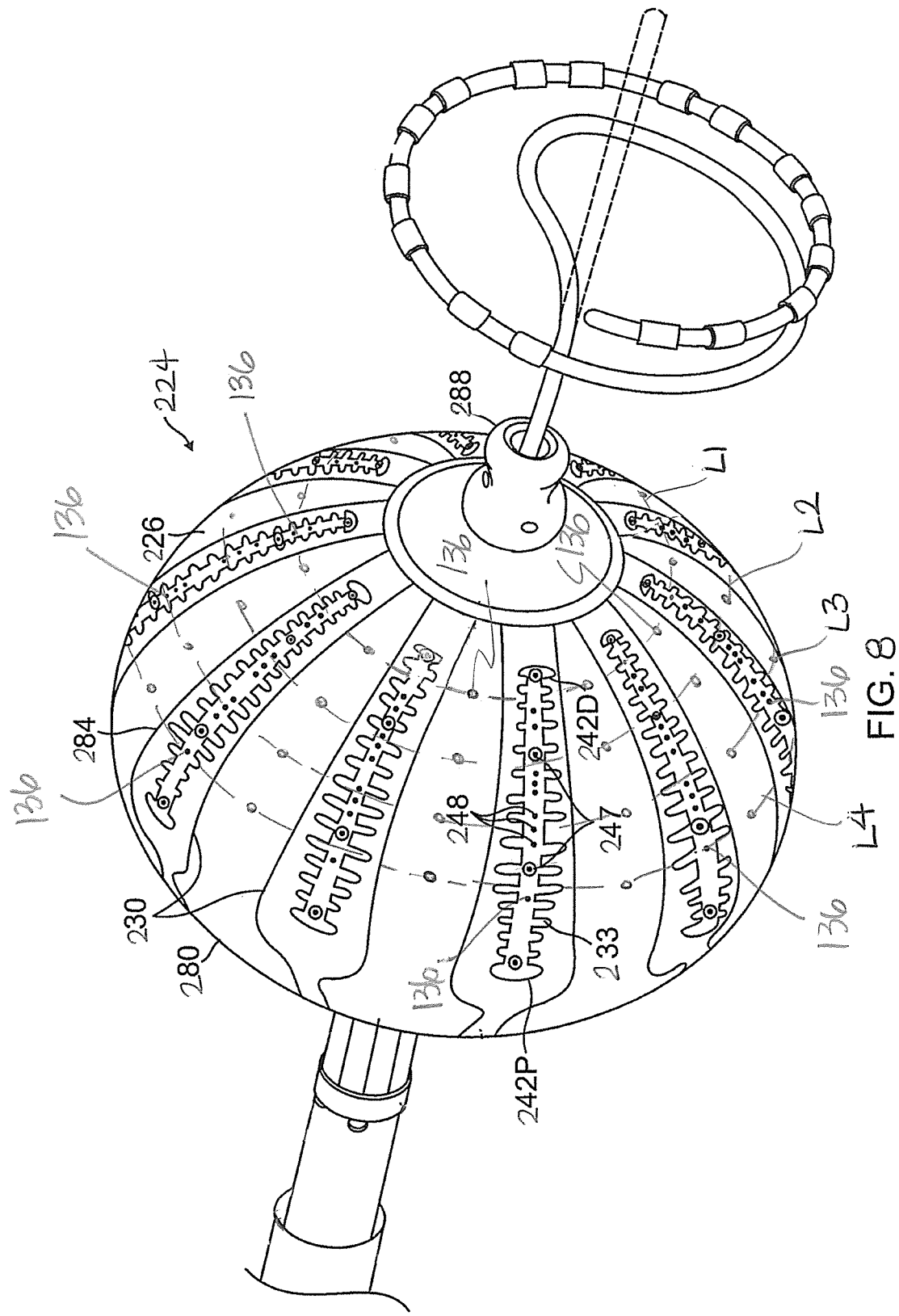
FIG. 8 is a perspective view of a balloon of the balloon catheter of FIG. 7, along with a lasso catheter inserted therethrough.
Figure 11:
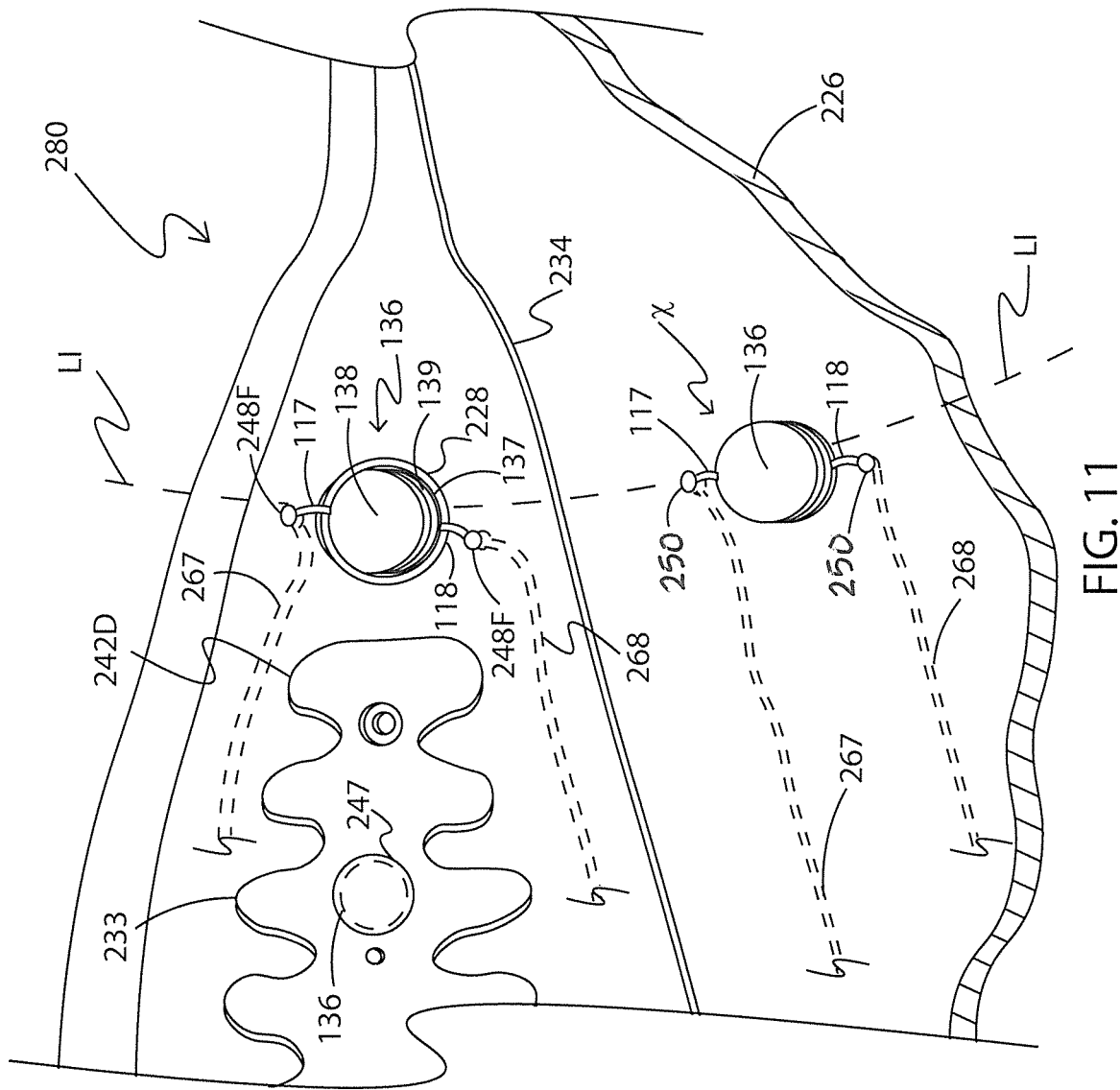
FIG. 11 is a detailed perspective view of a balloon membrane with capacitive force sensors, according to an embodiment of the present invention.

In some embodiments, one or more substrates 234 of the balloon 280 each include at least one capacitive force sensor 136 strategically positioned at predetermined locations between the equator and the distal end of the balloon 280, for example, generally along one or more latitudes, e.g., L1, L2 and L3, of the balloon 280 as shown in FIG. 8, for circumferential contact with an ostium or tubular region. For example, a capacitive force sensor 136, with plates 137 and 138 and a dielectric 139 therebetween, may be positioned generally along a latitude L1 distal of each contact electrode 233, as shown in FIG. 11. In some embodiments, each capacitive force sensor 136 has its plate 138 affixed to the outer surface 234 of the membrane 226, situated within a through-hole 228 formed in the respective substrates 234 of the contact electrodes 233. (In some embodiments, the plate 138 may be affixed to the membrane 226.) Terminals 117 and 118 for each respective capacitive force sensor 136 are each connected to a respective full via 248F that includes conductive formation that extends through a through-hole (not shown) in the respective substrates 234 and the membrane 226 to connect to respective lead wires 267 and 268, respectively, that extend into the interior of the balloon 280 and toward the proximal end of the balloon and through the shaft 270. It is understood that the lead wires may be included in a ribbon cable that extends through the interior of the balloon 280. In some embodiments, capacitive force sensor 136 (shown in broken lines in FIG. 11) may be provided within an exclusion zone 247' formed in the contact electrode 233.

In some embodiments, one or more capacitive force sensors 136A are affixed at predetermined locations X on the membrane 226 along one or more latitudes, with the plates 138 affixed to the membrane 226, as shown in FIG. 11. Terminals 117 and 118 for each respective capacitive force sensor 136 are each passed through a respective through-hole formed in the membrane 226, sealed by plugs 250, into the interior of the balloon 280 toward the proximal end of the balloon and through the shaft 270. In some embodiments, lead wires 267 and 268 may be connected to terminals 117 and 118, respectively, in the interior of the balloon 280.

It is understood that in some embodiments, the dielectric 139 between the plates 137 and 138 may be air, and that an elastic spring member 148, e.g., wave spring, may be situated between the plates (FIG. 12) to support the plates at a separation distance D therebetween, where the spring member 148 is elastically compressible to allow the separation distance D to decrease when a contact force is applied to the plates upon tissue contact.

It is also understood that in some embodiments, the capacitive force sensor are formed by 3-D printing, including 3-D printing directly onto the catheter distal tip surface on which the sensor is carried on the catheter, and that 3-D printing may be used to form the plates, as well as any mechanical spring for separating and support the plates.

In use, the capacitance of the force sensor 136 is measured by the force sensing module 53 (see FIG. 1). The capacitance for the force sensor 136 in the neutral state with the plates 237 and 238 separated by a distance D is measured by the force sensing module 53 as C. As the balloon 280 approaches an ostium, a distal circumferential portion of the balloon comes into contact with the ostium which exerts a force with a normal force component N that compresses the dielectric 239 changing the separation distance from D to D1, where D1<D, which changes the capacitance of the force sensor 136 from C to C1, where C1>C. The force sensing module 53 detects the increase capacitance C1 and, for example, responds by providing an indicia to the medical professional 14, such as sounding an audio signal or a visual signal. The measured capacitance remains at C1 so long as the normal force component N remains. Where the normal force component increases (such as where the medical professional further presses the balloon 280 against the ostium), the separation distance decreases further to D2 where D2<D1<D and the measured capacitance increases correspondingly to C2, where C2>C1>C. Where the normal force component decreases (such as where the medical professional slightly retracts the balloon from the ostium, the separation distance increases to D3 where D1<D3<D, measured capacitance decreases correspondingly to C3, where C1>C3>C. In this manner, the change in the capacitance output of the force sensors 236 detected and measured by the force sensors 236 advantageously indicates the change in force applied to the tip electrode 105 reflective of the change in tissue contact between the balloon and the ostium. Different readings or different changes in readings by the force sensing module of the capacitive force sensors along one or more latitudes of the balloon can indicate the angle of contact, e.g., off-axis tilt angle of the longitudinal axis of the balloon relative to the longitudinal axis of the ostium. For example, where contact is sensed by x numbers of capacitive force sensors along latitude La and contact is sensed by y numbers of capacitive force sensors along latitude Lb, where x≠y, a system processing these signals could provide an indicator of an inference to user that the longitudinal axis of the balloon is not aligned with the longitudinal axis of the ostium.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiology catheter system comprising:
  a catheter comprising:
    an elongated catheter body; and
    a distal tip electrode comprising:
      an electrode shell with a shell wall configured with a recess; and
      a capacitive force sensor including an inner conductive plate, an outer conductive plate, and a compressible dielectric therebetween, the inner conductive plate disposed in the recess, the outer conductive plate movable relative to the inner conductive plate between a neutral position and a tissue contact position, the outer conductive plate in front of the shell wall at a distance D from the inner conductive plate when the outer conductive plate is in the neutral position, the outer conductive at a distance D1 from the inner conductive plate when the outer conductive plate is in the tissue contact position, the distance D1 less than the distance D;
  a processor having a memory device and a voltage source;
  a first terminal connected to the outer conductive plate and the voltage source; and
  a second terminal connected to the inner conductive plate and the voltage source;
  wherein the memory device is configured to store instructions that, when executed by the processor, causes the processor to:
    activate the voltage source;
    detect a change in capacitance across the capacitive force sensor when the outer conductive plate moves from the distance D to the distance D1; and
    determine a force applied by distal tip electrode against tissue based on the change in capacitance.

2. The system of claim 1, wherein the shell has a distal wall and the recess is formed in the distal wall.

3. The system of claim 1, wherein the shell has a circumferential wall and the recess is formed in the circumferential wall.

4. The system of claim 1, wherein the recess includes a stamped recess.

5. The system of claim 1, wherein the recess includes a shallow bored recess.

6. The system of claim 1, wherein the first terminal extends through an interior of the shell.

7. The system of claim 6, where the distal tip electrode includes a plug at a proximal end of the shell, the first terminal extends through a through-hole configured in the plug.

8. The system of claim 1, wherein the second terminal extends through an interior of the shell.

9. The system of claim 8, wherein the distal tip electrode includes a plug at a proximal end of the shell, the second terminal extends through a through hole configured in the plug.

10. The system of claim 1, wherein the outer conductive plate, the dielectric and the inner conductive plate have a combined thickness and the recess has a depth that is less than the combined thickness, such that at least outer conductive plate is projected out in front of the shell when the capacitive force sensor is in a neutral state.

11. The system of claim 1, further comprising a flex circuit, the flex circuit including the first and second terminals.

12. The system of claim 11, wherein the flex circuit extends along an outer surface of the shell.

\* \* \* \* \*